United States Patent [19]

Gillette

[11] Patent Number: 4,820,519
[45] Date of Patent: Apr. 11, 1989

[54] METHOD AND COMPOSITION FOR STORAGE OF PLANT MATERIAL

[75] Inventor: Paul C. Gillette, Wilmington, Del.

[73] Assignee: Hercules Incorporated, Wilmington, Del.

[21] Appl. No.: 134,286

[22] Filed: Dec. 17, 1987

[51] Int. Cl.$^4$ ................ A01N 25/34; A61K 9/70
[52] U.S. Cl. .................... 424/412; 424/78; 424/409; 424/416; 424/443; 514/529; 264/210.6; 264/211
[58] Field of Search .............. 427/4; 424/78, 401, 424/412, 416, 443; 264/210.6, 211; 514/529

[56] References Cited

U.S. PATENT DOCUMENTS

Re. 32,356  2/1987  Candarelli ................ 414/81 X
4,514,406   4/1985  Ohsumi et al. ............ 514/352
4,725,607   2/1988  Perrior et al. ........... 514/345

Primary Examiner—Michael Lusignan
Attorney, Agent, or Firm—David Edwards

[57] ABSTRACT

Plant material such as tobacco is protected during storage by enveloping the plant material in a thin film that is composed of a polymeric material and isopropyl-(E,E)-11-methoxy-3,7,11-trimethyl-2,4-dodecadienoate (hereinafter referred to as "methoprene"). Air moves within the envelope carrying methoprene that has migrated from the surface of the film to the surface of the plant material. The thin film is a biaxially oriented polyolefin that has a thickness of from 0.01 to 0.2 mm and has from about 100 to 20,000 ppm of said methoprene incorporated therein.

7 Claims, 2 Drawing Sheets

METHOD AND COMPOSITION FOR STORAGE OF PLANT MATERIAL

The invention relates to a method and composition for storing plant material. More particularly, the invention provides a film useful for controlling insects during storage of plant material such as tobacco.

The protection of plant material, such as tobacco, during storage from destruction by insects such as cigarette beetles and tobacco moths is an important area of concern for the tobacco industry. Once a hogshead of tobacco becomes infested with insects, they multiply at an exponential rate, consuming the tobacco. A number of methods have been proposed in an effort to minimize this destruction. Until relatively recently, the approaches involved periodic exposure of the tobacco to some toxic compound. Recently, spraying of stored tobacco with low levels of isopropyl-(E,E)-11-methoxy-3,7,11-trimethyl-2,4-dodecadienoate (hereinafter referred to as "methoprene") has been shown to provide an effective means of controlling insects.

The present invention beneficially effectively controls insects during tobacco storage using less methoprene than the spray method. This reduces the storage cost and the concentration of residual methoprene in the tobacco product.

Controlled release of compounds such as pesticide utilizing a polymer matrix floating in water is discussed by Cardarelli, in U.S. Pat. No. Re 32,356. Note column 5, lines 67–68 and column 6, lines 1–16. Quinn, in U.S. Pat. No. 4,666,747, discloses a spray method and formulation for use therein. The active ingredient may be methoprene, which is known to prevent larval forms of the cigarette beetle and tobacco moth from developing into normal pupae, or adults. It is applied in ethanol: water solvent (10 ppm active ingredient), note column 7, lines 43–53. Isaka, et al., in U.S. Pat. No 4,230,767, discloses a propylene polymer for external packaging of products including tobacco and provides insect proofness, note column 1, lines 20–17. Ohsumi, et al., in U.S. Pat. No. 4,514,406, discloses oxide ethers having juvenile hormone-like controlling effect, like methoprene. Methods of making methoprene are disclosed in U.S. Pat. Nos. 3,904,662 and 3,912,815. Hymen, at al. in U.S. Pat. No. 3,864,468 discloses activated polymer materials. Polyvinyl chloride film coated with an antibacterial is used to inhibit bacterial growth.

SUMMARY

A method and composition for storing plant material such as tobacco. A film is provided which includes polymeric material and methoprene. Tobacco is then positioned within an enclosure formed by the film. The film has a thickness of from 0.01 to 0.2 millimeters, and has from 100 to 20,000 ppm of methoprene per gram of polymeric material. Air moves within the enclosure carrying methoprene from the surface of the film to the surface of the tobacco.

DETAILED DESCRIPTION OF THE INVENTION

The present invention provides a method of storing plant material, such as tobacco or grain, for example wheat. In a preferred embodiment, tobacco is enclosed by a polymeric film having a thickness of from 0.01 to 0.2 millimeters, and 0.16 to 20 mg methoprene per gram of the polymeric material.

The method of the invention provides a film for insect control. Plant material stored within the film of the present invention is protected from attack by insects. The plant material need not be sprayed to control attack from insects and the concentration of insect control agent required for effective insect control using the film is lower than the concentration of methoprene required to control insects using the prior art spray method.

In accordance with the present invention, fine granules of polymeric material are mixed with methoprene and the mixture extruded into a thin film having a thickness of from 0.01 to 0.2 millimeters. The polymeric material is a thermoplastic polymer for example, polypropylene or polyethylene. In a preferred embodiment of the invention, methoprene in the film product results from the addition of from 0.16 to 20 milligrams of methoprene for each gram of polymeric material in the film. Optimum concentrations depend upon film thickness and storage conditions such as time and temperature.

Most preferably, the polymeric film used in accordance with the invention is from 0.1 to 0.2 millimeters thick. Preferably, the polymeric film used in accordance with the invention is polypropylene, polyethylene or polyester. The film is preferably made by casting methoprene onto a film, extruding a film from a mixture of polymer and methoprene. Preferably, cast sheets of the film are biaxially oriented to improve mechanical properties. In addition, the methoprene may be introduced into the film through the use of supercritical fluid techniques.

In a preferred embodiment of the invention, the roll of polymer film having a coating of at least 23 mg per square meter of methoprene is heated to 200° F. for 30 minutes in an enclosure to cause methoprene to migrate into the film.

Figure 1:
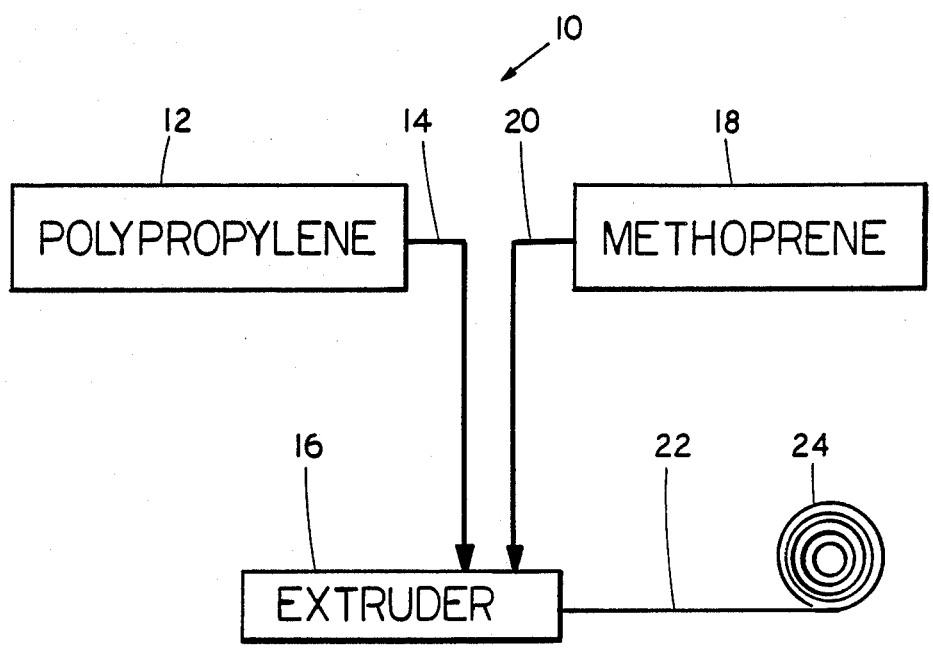
FIG. 1 is a schematic diagram of a system for making film useful in accordance with the invention.

The invention is now described with reference to the Figures wherein the same numeral in each figure refers to the same item. With more particular reference to FIG. 1, a system for making film is shown generally at 10. Polypropylene from the polypropylene container 12 is conveyed through line 14 to extruder 16. Methoprene from methoprene container 18 is conveyed through line 20 to extruder 16. Methoprene impregnated film 22 is extruded from extruder 16. The film 22 is wound onto film roll 24 for convenient storage and transportation.

Figure 2:
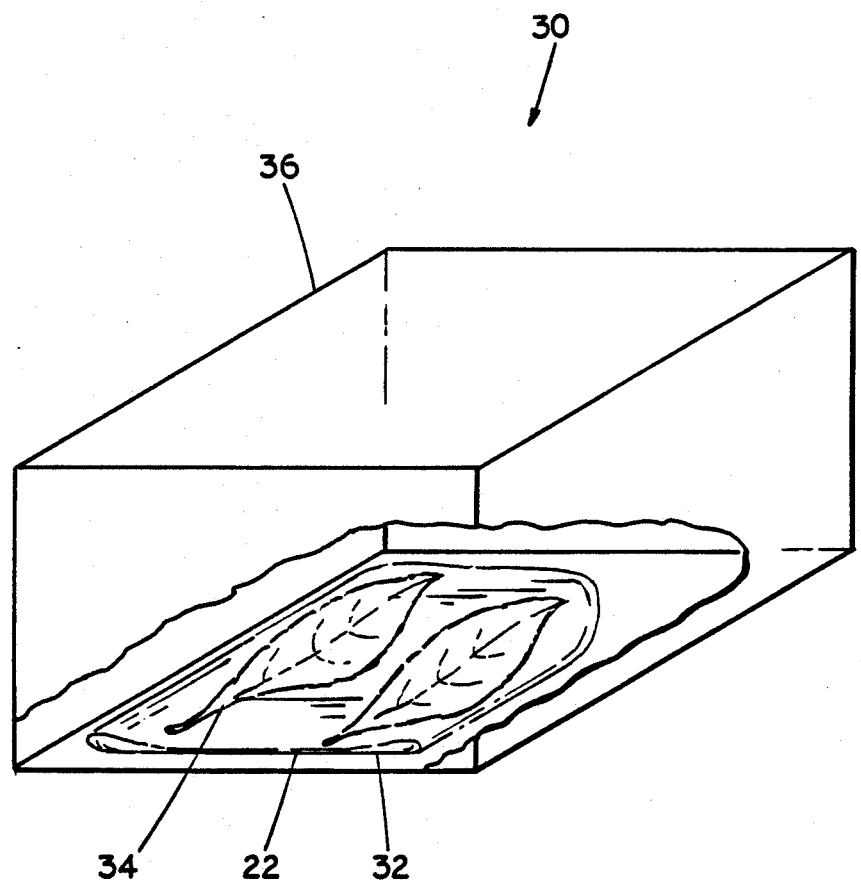
FIG. 2 is a perspective view of tobacco stored in film in accordance with the invention.

With more particular reference to FIG. 2, a tobacco storage system is shown generally at 30. The enclosure 32 is made of methoprene impregnated film 22. Methoprene slowly migrates out of the film and collects within the enclosure 32. The concentration of methoprene in the film 22 is sufficient to prevent insects from chewing therethrough. This makes enclosure 32 effective to control attack by insects of plant material, such as tobacco 34.

EXAMPLE 1

1 kilogram of polypropylene granules and 10 grams of methoprene are dry blended and fed to a film extruder. The mixture is extruded as 0.75 millimeter thick film, which is subsequently biaxially oriented to six times its original length and six times its original width at 145° C. by a film stretcher. 1 Kilogram of tobacco leaves are wrapped in 3.5 grams of the methoprene containing polypropylene film and stored. 1 Kilogram of tobacco leaves are wrapped in 3.5 grams of polypropylene film not containing methoprene and stored. After two months, the tobacco wrapped in untreated film shows appreciable insect destruction. The tobacco wrapped in treated film shows no insect destruction.

EXAMPLE 2

1 kilogram of polypropylene granules and 5 grams of methoprene are dry blended and fed to a film extruder. The mixture is extruded as 0.1 millimeter thick film. 1 Kilogram of tobacco leaves is wrapped in 17 grams of the methoprene containing polypropylene film and stored. 1 Kilogram of tobacco leaves is wrapped in 17 grams of polypropylene film not containing methoprene and stored. After two months, the tobacco wrapped in film shows appreciable insect destruction. The tobacco wrapped in methoprene containing film shows no insect destruction.

EXAMPLE 3

1 kilogram of polypropylene granules and 20 grams of methoprene are mixed and fed to a film extruder. The mixture is extruded as 0.05 millimeter thick film. 1 Kilogram of tobacco leaves is wrapped in 8.5 grams of the methoprene containing polypropylene film and stored. 1 Kilogram of tobacco leaves is wrapped in 8.5 grams of polypropylene film not containing methoprene and stored. After two months, the tobacco wrapped in film shows appreciable insect destruction. The tobacco wrapped in methoprene containing film shows no insect destruction.

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A method of protecting plant material from insect attack during storage comprising enclosing said plant material in a film of polymeric material of from 0.01 to 0.2 mm thick and an effective amount of isopropyl-(E,E)-11-methoxy-3,7,11-trimethyl-2,4-dodecadienoate in the polymeric material to inhibit insect attack of the plant material wherein air moves within the envelope carrying isopropyl-(E,E)-11-methoxy-3,7,11-trimethyl-2,4-dodecadienoate that migrates from the surface of said film to the surface of said plant material.

2. The method of claim 1 wherein the polymeric material is selected from polypropylene, polyethylene, or polyester.

3. The method of claim 2 wherein the polymeric material is a biaxially oriented polypropylene.

4. The method of claim 2 wherein the plant material is tobacco.

5. The method of claim 4 wherein the effective amount is from 100 to 20,000 ppm of isopropyl-(E,E)-11-methoxy-3,7,11-trimethyl-2,4-dodecadienoate per gram of polymeric material.

6. A film product comprising polymeric material and from 0.10 to 20 mg of isopropyl-(E,E)-11-methoxy-3,7,11-trimethyl-2,4 dodecadienoate per gram of polymeric material, said film product having a thickness of from 0.01 to 0.2 mm and being biaxially oriented.

7. The film product of claim 6 wherein the polymeric material is selected from polypropylene, polyethylene, or polyester.

* * * * *

UNITED STATES PATENT AND TRADEMARK OFFICE
CERTIFICATE OF CORRECTION

PATENT NO. : 4,820,519
DATED : APRIL 11, 1989
INVENTOR(S) : GILLETTE

It is certified that error appears in the above-identified patent and that said Letters Patent is hereby corrected as shown below:

Column 2, Line 8

"0.16" should read --including 0.10--

Column 2, Line 25

"0.16" should read --0.10--

Column 4, Line 34

"film product" should read --film--.

Signed and Sealed this

Third Day of October, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,820,519

DATED : APRIL 11, 1989

INVENTOR(S) : Paul C. Gillette

It is certified that error appears in the above-identified patent and that said Letters Patent is hereby corrected as shown below:

<u>Column 1, Line 43</u>

"lines 20-17" should read --lines 20-27--

<u>Column 1, Line 48</u>

"at al" should read --et al--.

Signed and Sealed this

Sixth Day of February, 1990

*Attest:*

JEFFREY M. SAMUELS

*Attesting Officer*   *Acting Commissioner of Patents and Trademarks*